United States Patent [19]
Edens et al.

[11] Patent Number: 6,013,255
[45] Date of Patent: Jan. 11, 2000

[54] STABLE WATER-IN-OIL EMULSIONS

[75] Inventors: Luppo Edens, Rotterdam; Dirk Meijer, Breda; Petrus Andreas Van Paridon, Voorburg, all of Netherlands

[73] Assignee: Gist-brocades B.V., Netherlands

[21] Appl. No.: 08/978,543

[22] Filed: Nov. 26, 1997

Related U.S. Application Data

[63] Continuation of application No. 08/564,101, Apr. 8, 1996, abandoned.

[30] Foreign Application Priority Data

Apr. 18, 1994 [EP] European Pat. Off. .............. 94201067

[51] Int. Cl.[7] .......................... A61K 9/107; A61K 38/43
[52] U.S. Cl. ...................... 424/94.1; 424/439; 436/601; 436/602
[58] Field of Search ................. 424/78.08, 440, 424/94.1, 439

[56] References Cited

U.S. PATENT DOCUMENTS

| | | |
|---|---|---|
| 3,958,033 | 5/1976 | Sims et al. . |
| 3,966,632 | 6/1976 | Colliopoulos et al. . |
| 4,869,919 | 9/1989 | Lowery . |
| 4,985,173 | 1/1991 | Takahashi et al. ...................... 252/314 |
| 5,085,856 | 2/1992 | Dunphy et al. ........................... 424/64 |
| 5,306,517 | 4/1994 | Norton et al. ........................... 426/602 |

FOREIGN PATENT DOCUMENTS

| | | |
|---|---|---|
| 0174377 | 10/1985 | European Pat. Off. . |
| 0 174 377 | 3/1986 | European Pat. Off. . |
| 0 247 552 | 12/1987 | European Pat. Off. . |
| 0 354 356 | 2/1990 | European Pat. Off. . |
| 56-45405 | 4/1981 | Japan . |
| 64-63032 | 3/1989 | Japan . |
| 5-86368 | 4/1993 | Japan . |
| 562281 | 9/1977 | U.S.S.R. . |
| 9206599 | 4/1992 | WIPO . |
| WO 92/06599 | 4/1992 | WIPO . |
| 9316175 | 8/1993 | WIPO . |
| WO 93/14645 | 8/1993 | WIPO . |
| WO 93/16175 | 8/1993 | WIPO . |

OTHER PUBLICATIONS

Lillehaug, A., "Oral immunization of rainbow trout, *Salmo gairdneri* Richardson, against vibriosis with vaccines protected against digestive degradation," *Journal of Fish Diseases* 1989, 12, 579–584.

Abstract of Japan 50–86368.

*Primary Examiner*—Peter F. Kulkosky
*Attorney, Agent, or Firm*—Morrison & Foerster LLP

[57] ABSTRACT

The present invention describes stable water-in-oil emulsions comprising the following components: water, oil, a labile compound of interest, a stabilizing agent and an emulsifier. The labile compound present in the water phase is stabilized by addition of a stabilizing agent which preferably is a polyol. Specific emulsifiers are described which give rise to stable emulsions in the presence of high amounts of a polyol.

8 Claims, No Drawings

STABLE WATER-IN-OIL EMULSIONS

This application is a continuation of application Ser. No. 08/564,101, filed Apr. 8, 1996, now abandoned.

TECHNICAL FIELD

The present invention describes stable water-in-oil emulsions. The emulsions are used to add labile compounds to feed, food or cosmetic compositions.

BACKGROUND OF THE INVENTION

Several additives for food, feed and cosmetics are regarded labile, such as colourants, vitamins, vaccines or enzymes.

Additives can be chemically or enzymatically incompatible with other compounds present in a composition. Otherwise, additives can be heat labile and therefore tend to be deactivated during processing steps which occur at an elevated temperature. For example, feed or food is often prepared by using an extrusion process. These extrusion processes are necessary for obtaining food or feed particles in the required shape. Furthermore, there is a growing tendency to include all sorts of additives to a basic feed or food. Feed or food compositions are more often prepared complete with additives which previously used to be added independently.

Several solutions have been suggested to overcome degradation of a labile compound. One solution is the addition of the desired compounds subsequent to a process step at elevated temperature, e.g. after the extrusion process. Different reports have been published concerning formulations of labile compounds and/or for methods to add such compounds to feed or food particles.

DE 2602260 describes the use of a suspension of an enzyme in a liquid or a molten edible fat. After cooling of the mixture the material has to be particularized. After rough destruction the particles are further treated for example by milling. This process has the disadvantage that the milling of powders to guarantee a small particle size is very tedious and leads to undesirable dusts.

International Patent Application WO 93/14645 solves the problem by addition of an oil suspension containing the heat-labile compounds after the extrusion process. The addition of the suspension to the pellets is performed under lowered pressure.

International Patent Application WO 92/06599 describes the use of a water-in-oil emulsion for protecting vaccines. There is no mentioning of the use of a (protein) stabilizing (i.e. a water activity lowering) agent as part of the emulsion. The formulation of labile compounds such as enzymes in such an emulsion would give rise to a rapid loss of enzymes activity. This loss may amount to 50% per month in hot climates which is unacceptable for commercial products. This patent application also describes the preferred application of a lecithin-based emulsifier.

International Patent Application WO 93/16175 describes a stabilized, aqueous enzyme solution comprising urea and/or a polyol as stabilizing agent. Urea and polyols are known agents to stabilize an enzyme in an aqueous environment.

In the area of cosmetics there also is a growing tendency to include labile compounds in oil containing end products. Especially compounds aimed at skin protection, cleansing and rejuvenation are of obvious interest. Labile compounds claimed to have beneficial effects in this respect include enzymes, such as proteases.

To guarantee enzyme activity in cosmetic formulations over extended shelf life periods, essentially water-free, hydrophobic compounds such as waxes, plant or mineral oils commonly are used as enzyme formulation agents. Although this approach implies a high storage stability of the enzyme in the cosmetic formulation, a serious disadvantage is that the enzyme can only be activated by exposing the formulations to relatively large quantities of water (during which the initially water-free enzyme, is dissolved). An inherent problem is that enzyme activation is relatively slow and that much of the initial enzyme activity is wasted. This approach is not very convenient in several cosmetic applications.

In an alternative approach as described in J03004791, protein decomposing enzymes to be used in cosmetics are stabilized by adding polysaccharides to aqueous solution of the enzymes. Although this approach minimises the use of water needed to re-activate the enzyme, the approach disregards the need for a lipophilic phase in many cosmetic formulations.

SUMMARY OF THE INVENTION

The present invention discloses stable water-in-oil emulsions. Specifically, the present invention discloses a water-in-oil emulsion characterized in that it comprises the following components: water, oil, a labile compound of interest, a stabilizing agent and an emulsifier.

The water-in-oil emulsions of the present invention comprise a labile compound of interest dissolved in the water phase and stabilized by addition of a stabilizing agent. Preferably, the stabilizing agent is a water activity lowering agent. More preferably, the stabilizing agent is a polyol.

The polyol is added to the water phase of the water-in-oil emulsion in high concentrations, i.e. in amounts of at least 10%, preferably in amounts of 10–70%, more preferably in amounts of 30–70% (w/w).

A preferred composition comprises a water-in-oil emulsion containing a labile compound of interest in the water phase together with a polyol, and wherein the emulsion is stabilized using an emulsifier which is active at high concentrations of the polyol. The emulsifier which is used preferably is a distilled monoglyceride or polyglycerol polyricineolate.

Furthermore, the compound of interest preferably is an enzyme, a vitamin, a colourant or a vaccine.

The presented emulsions are used to protect labile compounds before addition to food, feed, cosmetic or oily compositions.

The water-in-oil emulsions of the present invention are stable for prolonged periods of time. They can be used for the preparation of human or animal food compositions. For instance, the water-in-oil emulsions of the present invention are sprayed on feed or food particles. Preferably, the emulsions are sprayed on feed or food particles after dilution of the emulsion in an oil or fat. In addition, the emulsions of the present invention can be used for the preparation of cosmetic compositions.

DETAILED DESCRIPTION OF THE INVENTION

The present invention discloses a water-in-oil emulsion containing in the water phase a compound of interest which is labile together with a stabilizing agent, and wherein the emulsion is stabilized using a suitable emulsifier.

The water-in-oil emulsion comprises the following components: water, oil, a labile compound of interest, a stabilizing agent and an emulsifier. The labile compounds are present in the water phase. The stabilizing agent is added to the water phase to stabilize the desired compound.

The labile compound can be any compound which is chemically or enzymatically incompatible with other compounds. An incompatible compound can be present either in the emulsion or in the composition to which the emulsion is added. In addition, the labile compound can be any compound which is heat labile.

The present invention discloses stable water-in-oil emulsions comprising more than one labile compound in the water phase. The present invention also discloses stable water-in-oil emulsions comprising a labile compound and a compound incompatible with the labile compound in the water phase. The present invention enables the preparation of emulsions comprising mutually incompatible, water-soluble compounds. The physical separation of these incompatible compounds is advantageously accomplished by their incorporation in individual water droplets in the oil phase of the emulsion.

Preferably, the labile compound comprises life microorganisms, which can be used for instance as a probiotic. More preferably, the labile compound is an enzyme, a vitamin, a colourant or a vaccine. Suitable enzymes include proteases, phytases, carbohydrases, lipases, phospholipases and oxidoreductases. Suitable vitamins include water-soluble vitamins, e.g. vitamin C.

The emulsions of the present invention are especially useful to formulate mutually incompatible compounds, e.g. enzyme mixtures of which one of the enzymes is a proteolytic enzyme.

Furthermore, the emulsions of the present invention enable an exact dosage of labile compounds. First of all because stability of the labile compounds is guaranteed, additionally because dosage of a liquid emulsion, in particular of an emulsion diluted in oil, is more precise than dosage of a powder. For instance, it is known that during the processing of feed, factors like heat, pressure, humidity, redox reactions and friction can have a dramatic impact on the stability of vitamins. Especially vitamins E, K and C (ascorbic acid) are known for their instability (see for example M. B. Coelho, Feed International, December 1991, page 39–45). Ascorbic acid is water soluble and known to be extremely sensitive to trace minerals which are commonly added to feed, such as iron. The incorporation of ascorbic acid into the water phase of a water-in-oil emulsion according to the present invention is an attractive option to minimise costly overdosage of the vitamin.

The water-in-oil emulsions of the present invention contain a water phase containing the desired compound in a highly concentrated form. The desired compound can be added to the water phase in an amount of 0.01–30% (w/w) on basis of the dry weight of the active compound.

The labile compounds are stabilized by the addition of a stabilizing agent to the water phase. Preferably, a water activity lowering agent is used as a stabilizing agent. The water activity lowering agent preferably is a salt, more preferably a polyol. Polyols that are particularly useful are glycerol, sorbitol, sucrose, polypropylene glycol, trehalose, maltodextrins, lactose and glucose.

In addition, the water activity lowering agent will act to prevent microbial growth in the water phase of the emulsion. If required, the microbial stability of the water phase can be further enhanced by incorporation of generally accepted (foodgrade) antimicrobial agents, such as sorbates or benzoates.

The amount of a water activity lowering agent to be added to the water phase depends on the amount of the agent which is required to obtain the desired stabilizing or the desired antimicrobial effect. Polyols are added to the water phase in amounts of at least 10%, preferably in amounts of 10–70%, more preferably in amounts of 30–70% (w/w).

To obtain stable emulsions, an emulsifier is used. Emulsifiers are surface-active substances which allow one liquid phase to be dispersed in another liquid phase. Emulsifiers possess both hydrophilic and lipophilic groups, the ratio of these groups is known as the HLB value.

In general, fat-soluble, hydrophobic emulsifiers have HLB values in the range of 0–9, while water-soluble substances have HLB values between 11 and 20. Suitable emulsifiers or mixtures of emulsifiers for stabilizing water-in-oil emulsions are claimed to have HLB values in the lower range.

Surprisingly, well known emulsifiers such as Span™ 80 (HLB=4.3), Tween™ 80 (HLB=15) and mixtures thereof do not give rise to stable water-in-oil emulsions in the presence of relatively high amounts of polyols. Lecithin-based emulsifiers, like Emulbesto™ 2000, Emulfluid™ E likewise result in fast phase separation.

The present invention for the first time describes emulsifiers which are active in the presence of relatively high amounts of polyols. Emulsifiers which work in the presence of amounts of polyols as high as 50% have been found.

Useful emulsifiers are monoglycerides (such as Hymono™ 1163 and Hymono™ 7804) and polyglycerol polyricinoleate (Admul™ WOL 1403). Due to the efficacy of the selected emulsifiers in the presence of relatively high amounts of polyols, coalescence of individual water droplets present in the oil phase is low. In this way, the emulsion according to the invention adequately prevents the migration of non-oil soluble compounds between individual water droplets in the emulsion.

Polyglycerol polyricinoleate (Admul™ WOL 1403) was found to be particularly useful in combination with phytase.

Polyglycerol polyricinoleate is liquid at room temperature and does not require heating up prior to or during mixing with oil. The viscosity of the emulsion remains low when using polyglycerol polyricinoleate and almost no droplet flocculation occurs. In addition, the use of polyglycerol polyricinoleate allows for a high concentration of the water phase in the emulsion.

Oils used in the emulsions of the present invention are the oils normally used in food, feed or cosmetic preparations. They include fish oil, soya oil, rapeseed oil, olive oil, cornflower oil, palm oil, avocado oil and different mineral oils.

The invention further discloses a method for the preparation of said water-in-oil emulsions.

The emulsions can be prepared by imput of a high amount of energy. For example by severe stirring or by applying high shearing forces. In this way, stable emulsions are obtained, which can be stably stored in this form.

The present invention discloses emulsions which are stable during a long storage time. The emulsions are stable for one month, more preferably for six months, most preferably for more than a year.

The water-in-oil emulsions according to the present invention can be employed as additives for food, feed or cosmetics.

The use of the emulsions of the invention enables food, feed or cosmetic manufacturers to apply labile compounds in process steps which would otherwise lead to deactivation of said labile compounds. Furthermore, the use of the emulsions of the invention adequately prevents the migration of non-oil soluble compounds from a feed, food or cosmetic composition to the water phase of the emulsion. In this way, the labile compound(s) of interest present in the water phase of the emulsion is/are adequately protected against chemical or enzymatical incompatibilities present in the composition to which the emulsion is added.

The emulsions of the present invention are used in the preparation of human or animal food or feed particles, especially in the preparation of particles for fish or poultry feed. Preferably, the emulsions are added by spraying on food or feed particles. The addition can also be performed under reduced pressure, as described in International Patent Application WO 93/14645.

The emulsions can be used as such to apply to the food or feed particles. Preferably, the emulsions are diluted in an oil or fat before addition to the food or feed particles. An advantage of this process is that the concentrated labile compound can easily, that is with low energy input, be homogeneously mixed with the oil phase. In this way an even distribution of the active compound in the oil is guaranteed. The oil, which then contains the diluted desired compound can subsequently be sprayed on the food or feed particle. This process requires a minimal investment in preparing the final mixture to be sprayed on the particles.

In another application the emulsion of the present invention can be used to improve the degumming of soy and rapeseed oil. In this case the emulsion is containing phospholipase A2. Degumming is the removal of lecithin from the indicated oils. The use of phospholipase for degumming has been extensively described in EP 0 513 709. This enzyme improves the water solubility of non-hydratable phospholipids, improving their removal from the oil. The water-in-oil emulsions of the present invention facilitate the addition of the phospholipase to the indicated oils.

Below some examples are presented, which only function to illustrate the present invention and in no way are meant to limit its scope.

EXAMPLE 1

Physical Stability of Water-in-oil Emulsions Using Different Emulsifiers and Different Enzymes 1a. Composition of enzyme solutions Stabilities of the various water-in-oil emulsions were demonstrated using a food-grade, neutral protease and a feed-grade phytase.

The standard solution of the protease contained 20 g of Protease B500 (Gist-brocades, Holland) dissolved in 80 g of water. After complete dissolution, either sorbitol or glycerol was added and dissolved to reach the designated concentration.

The standard solution of phytase contained either the raw fermentation concentrate (Natuphos® UF concentrate, obtained by ultrafiltration of a germ-free Aspergillus culture filtrate) or the standardized fermentation product Natuphos® 5000 (Gist-brocades, Holland) containing 40% sorbitol. The phytase solutions used in the various experiments contained glycerol or sorbitol in end concentration between 35 to 50%.

1b. Emulsions prepared with Span™ 80/Tween™ 80 mixtures

To 5 g of fish oil (capelin oil as obtained from Skretting, Norway), 0.5 g of either Span™ 80 or Tween™ 80 emulsifier (both from Brocacef, the Netherlands) was added. Additionally, an emulsifier mix was prepared containing different ratios of the above prepared Span™ 80 and Tween™ 80 solutions. After thorough mixing, 0.18 g of one of the above-described stabilized enzyme solutions was added, followed by extensive vortexing.

All emulsions containing either protease or phytase in combination with one of the various Span™ 80 and/or Tween™ 80 emulsifiers showed separation of the oil and aqueous layer within a few hours at room temperature.

1c. Emulsions prepared with lecithin-based emulsifiers

Emulbesto™ 2000, Emulfluid™ E and VP627 are all lecithin-based emulsifiers and obtained from Lucas Meyer, Germany. Following the approach outlined under (1b), emulsions were prepared using 0.5 g of each of the above-mentioned lecithin-based emulsifiers. Within a few hours all emulsions prepared with these emulsifier products showed separation of the oil and aqueous layer.

1d. Emulsions prepared with monoglyceride emulsifiers

Hymono™ 1163 and Hymono™ 7804 were obtained from Quest, Holland.

Under gentle stirring 24 g of Hymono™ (a monoglyceride; E471) is dissolved in 700 g of fish oil at a temperature of 70° C. (Hymono™ 1163) or 50° C. (Hymono™ 7804). Subsequently, the solution is cooled down till at least 50° C. Using a high speed homogenator (Ultra Turrax), 200 g of enzyme solution is dispersed in the emulsifier-containing oil phase and the emulsion is cooled down to room temperature. After a period of a few days, the water phase showed very limited sedimentation only. This sedimentation could be minimised by addition of palmitic acid.

1e. Emulsions prepared with polyglycerol polyricinoleate

Admul™ WOL 1403 (polyglycerol polyricinoleate) was obtained from Quest, Holland. In combination with labile compounds this emulsifier has several advantages, a.o. the fact that Admul™ WOL 1403 is a liquid at room temperature which allows easy dissolution in the oil phase. This circumvents the need for heating up the oil, so that the handling is easier and the labile compounds can be added to the mixture of oil/emulsifier at room temperature, thereby minimising thermal stress.

To prepare an emulsion with Admul™ WOL 1403, 3 g of Admul™ WOL 1403 was mixed with 87.5 g of fish oil, followed by the addition of 25 g of Natuphos® 5000 (stabilized with 50% sorbitol). The viscosity of the emulsion remained low, the droplet size of the water phase was about 2 µ and no association of the droplets occurred. This indicates the excellent emulsifying property of Admul™ WOL 1403 in this system. The low viscosity allows a much higher concentration of the water phase containing the enzyme in the final emulsion.

By increasing the quantity of Admul™ from 3 g to 9 g, it appeared to be possible to emulsify a mixture of 75 g Natuphos® 5000 Liquid in 87.5 g fish oil. This emulsion is physically stable for a period of 6 months at least. With the phytase enzyme, the Admul™ emulsion is superior over the Hymono™ emulsions in terms of flocculation behaviour and is physically more stable than the Hymono™ emulsions (see Table 1).

Table 1. Comparison of the physical parameters and properties of the Hymono™ 1163 and Admul™ WOL 1403 emulsions.

| PHYSICAL PARAMETERS AND PROPERTIES | HYMONO 1163 | ADMUL WOL |
|---|---|---|
| temperature to dissolve the emulsifier | 70° C. | R.T. |
| temperature during addition of the enzyme | 50° C. | R.T. |
| energy to prepare the emulsion | high | low |
| viscosity of the emulsion | medium | low |
| droplet flocculation | medium | low |
| droplet size | 2–10µ | 2µ |
| maximal concentration of water phase in the emulsion | ca 22% (w/w) | ca 44% (w/w) |

EXAMPLE 2

Enzyme Activity in a Neutral Protease Water-in-oil Emulsion

Solution A:

Under gentle stirring 5 g of a spray dried Protease B500 preparation is dissolved in 20 g demi water. The protease solution is diluted with glycerol to obtain a final glycerol concentration of 50%.

Solution B:

Under gentle stirring 6 g of Hymono™ 1163 is dissolved in 175 g of fish oil at a temperature of 70° C. Subsequently, the solution is cooled down to 50° C.

Using a high speed homogenator, Solution A is dispersed in Solution B. The emulsion is cooled down to room temperature.

The protease activity of the protease water-in-oil emulsion is about 17,000 U/g emulsion. The recovery of protease from both Solution A and the water-in-oil emulsion was approximately 90%, which illustrates that emulsification has no significant detrimental effects on proteolytic activity. The storage stabilities of the emulsion kept at either 25° C. or 35° C. are shown in Table 2.

Table 2. Storage stability of the protease emulsion preparation.

| | PROTEOLYTIC ACTIVITY | | | | DROPLET DIAMETER | |
|---|---|---|---|---|---|---|
| | 25° C. | | 35° C. | | | |
| TIME | U*/g | | U*/g | | µ | |
| (week) | emulsion | % | emulsion | % | 25° C. | 35° C. |
| 0 | 16,926 | 100 | 16,926 | 100 | 2–10 | 2–10 |
| 1 | 12,078 | 71 | 14,719 | 87 | 2–10 | 2–10 |
| 2 | 19,957 | 118 | 17,446 | 103 | — | — |
| 3 | 17,056 | 101 | 14,892 | 88 | — | — |
| 4 | 15,281 | 90 | 14,113 | 83 | — | — |
| 5 | 14,848 | 88 | 12,468 | 74 | — | — |
| 6 | 15,844 | 94 | 7,143 | 42 | 2–10 | 2–10 |
| 7 | 13,420 | 79 | 10,736 | 63 | — | — |
| 5 (month) | — | — | — | — | 2–15 | — |

* A unit of protease activity is the amount of enzyme activity which produces an amount of hydrolysate from casein (Hammersten, Merck) at pH 7.0 and 37° C., having a similar optical density at 275 nm as a tyrosine solution of 1.5 µg/ml

EXAMPLE 3

Enzyme Activity in a Stable Phytase Water-in-oil Emulsion

Solution A:

Under gentle stirring 100 g sorbitol is dissolved in 100 g of Natuphos® UF-concentrate.

Solution B:

Under gentle stirring 24 g of Hymono™ 1163 is dissolved in 700 g of fish oil at a temperature of 70° C. Subsequently the solution is cooled to 50° C.

Using a high speed homogenator, Solution A is dispersed in Solution B. The emulsion is cooled down to room temperature.

The recovery of phytase activity from both Solution A and the phytase water-in-oil emulsion was approximately 90%. This illustrates that emulsification has no detrimental effects on the phytic acid degrading activities of the enzyme. Phytase activity was determined as described in EP 0 420 358.

The storage stabilities of the emulsion kept at either 25° C. or 35° C. are shown in Table 3.

Table 3. Storage stability of the phytase emulsion preparation.

| | PROTEOLYTIC ACTIVITY | | | | DROPLET DIAMETER | |
|---|---|---|---|---|---|---|
| | 25° C. | | 35° C. | | | |
| TIME | U*/g | | U*/g | | µ | |
| (week) | emulsion | % | emulsion | % | 25° C. | 35° C. |
| 0 | 531 | 100 | 531 | 100 | 2–10 | 2–10 |
| 1 | 623 | 117 | 569 | 107 | 2–10 | 2–10 |
| 3 | 494 | 93 | 654 | 123 | — | — |
| 4 | 616 | 116 | 528 | 99 | — | — |
| 5 | 523 | 98 | 337 | 63 | — | — |
| 6 | 513 | 97 | 451 | 85 | 2–10 | 2–15 |
| 7 | 295 | 56 | 380 | 71 | — | — |
| 5 (month) | — | — | — | — | 2–15 | — |

* A unit of phytase activity is defined as that amount of enzyme which liberates inorganic phosphorus from 1.5 mM sodium phytate at the rate of 1 µmol/min at 37° C. and at a pH of 5.50

EXAMPLE 4

Preparation of Stable Phytase and Protease Water-in-oil Emulsions Using Polyglycerol Polyricinoleate 4a. Phytase/oil emulsion Either 3.0 g or 9.0 g Admul™ W 1403 was dissolved in 87.5 g fish oil, whereupon an emulsion was prepared with 75.0 g Natuphos® 5000 containing 50% sorbitol, using an Ultra Turrax during 2* 30 seconds at full speed. The Natuphos® which was stabilized with 40% sorbitol has been brought to 50% using additional sorbitol. As a result, the calculated activity will be 4100 U/g instead of 5000 U/g.

The breaking of the emulsion:

The emulsion is slowly deep frozen until −20° C. and is kept at this temperature during 20 hours. Subsequently, it is brought to room temperature and centrifuged at 20,000 rpm in a Sorvall centrifuge (SM 24 rotor) for 30 minutes. During this treatment the temperature is 20–25° C.

The emulsion containing 3.0 g of emulsifier is now separated in 3 layers, i.e. a clear oil layer, a thin interphase and a clear water layer. In this water layer, phytase activity has been determined to be 3750 U/g, demonstrating that phytase activity has been recovered for at least 90%.

The emulsion containing 9.0 g of emulsifier could not be separated by centrifugation. Kept at room temperature, the latter emulsion remained physically stable for a period of 6 months at least. This observation is in accordance with the superior stability of the phytase emulsion described in Example 1.

4b. Protease/oil emulsion

A mixture of 87.5 g fish oil, 3.0 g Admul™ WOL 1403 (dissolved in fish oil) and 75.0 g Protease B500 in a solution of 50% sorbitol was homogenized in the same way as described above for the phytase/oil emulsion. Quite surprisingly, the combination of this proteolytic enzyme with the Admul™ WOL emulsifier generated emulsions which exhibited a decreased stability as compared to the stability of Protease B500 in combination with the Hymono™ emulsifier (see Example 2). Obviously, the Hymono™ emulsifier is to be preferred in preparing the protease B500 emulsions.

EXAMPLE 5

Stability of Phytase in Emulsions Containing Proteases

To demonstrate the protecting effect of the emulsion on incompatible compounds, water-in-oil emulsions containing both phytase and an acid protease were made. This example demonstrates that a mixture of emulsions containing either the phytase or the acid protease in an aqueous phase is more stable than an emulsion containing the two enzymes mixed in one aqueous phase.

Materials

Natuphos® UF concentrate (stabilized with 50% sorbitol by diluting a 70% sorbitol solution obtained from Roquette Frères, France).
Fromase® 150 TL (a liquid acid protease from Mucor miehei as obtained from Gist-brocades).
Admul™ WOL 1403 (from Quest, Holland).
Fish oil (capelin oil from Skretting, Norway)

5a. Natuphos®/oil emulsion

Following the protocol outlined in Example 4, a stable emulsion was obtained by dissolving 6 g Admul™ WOL in 87.5 g fish oil and subsequent vigorous mixing of the oil with 75 g Natuphos® UF concentrate. The emulsion was kept at 20° C. A first sample was immediately frozen at −20° C.

5b. Fromase®/oil emulsion

Two ml of Fromase® 150 TL were added to 98 ml water containing 50% sorbitol. The standard emulsion was prepared by mixing 87.5 g fish oil, 6 g Admul™ WOL and 75 g of the Fromase® solution. The emulsion was kept at 20° C.

5c. The mixed emulsion

Immediately after preparation of emulsions (5a) and (5b), a mixed emulsion was prepared by adding 100 ml of the Natuphos®/oil emulsion to 100 ml of the Fromase®/oil emulsion. After thorough handmixing, the mixture was stored at 20° C. A first sample was immediately frozen at −20° C.

5d. Natuphos®-Fromase®/oil emulsion

To 75 g of the Natuphos® UF concentrate with sorbitol 750 µl of Fromase® TL was added and then mixed. Addition of 87.5 g fish oil containing 6 g Admul™ WOL followed by vigorous mixing yielded the desired emulsion. The emulsion was stored at 20° C. A first sample was immediately frozen at −20° C.

5e. Stability of phytase in the various emulsions

Kept at 20° C., the various emulsions were sampled after 5 and 10 days of storage and immediately frozen at −20° C. After at least one night at −20° C., the various samples were thawed and centrifuged as described in Example 4. Phytase activities were determined by samples taken from the aqueous layer. Assuming 100% activity in the various samples obtained from the Natuphos®/oil emulsion (5a), the following phytase activities were recorded after 5 respectively 10 days of storage.

In the mixed emulsion (5c): 94% respectively 96% of the initial phytase activity.
In the Natuphos®-Fromase® oil emulsion (5d): 80% respectively 78% of the initial phytase activity.

Taking into account that the proteolytic activity of the Fromase® is relatively low due to the presence of the sorbitol, the data illustrate that the emulsion adds to the stability of formulated labile compounds. Phytase is protected against proteolytic attack when separately emulsified from the protease.

EXAMPLE 6

Stability of Vitamin C in Feed Containing Chemical Incompatibilities

Apart from the stabilizing effect observed in Example 5 using two incompatible enzymes in a single emulsion, a similar effect was observed in exposing vitamin C (ascorbic acid) to feed particles.

The incompatibility of ascorbic acid and trace minerals like copper and iron is well documented (see for example CRC Handbook of Food Additives, second edition, page 85 and further). However, nutritionists may advise combinations of both iron and ascorbic acid for certain feed application such as broiler finisher feed. This example demonstrates that ascorbic acid incorporated in an emulsion is significantly more stable than a non-emulsified ascorbic acid solution after mixing with broiler finisher feed pellets.

Materials

Soy oil (refined from OPG Farma, Holland)
Admul™ WOL 1403
Glycerol 86%
Citric acid (monohydrate p.a.)
Ascorbic acid (p.a.)
Broiler finisher feed (obtained from Arkervaart, Holland)

6a. Aqueous solution of ascorbic and citric acid

The water phase was prepared by dissolving 1 g citric acid and 4 g ascorbic acid in 45 g demi water. The pH of the aqueous mixture obtained was approx. 2.4. After complete dissolution, 50 g of glycerol was added and the mixture thoroughly mixed.

6b. Ascorbic acid/oil emulsion

Following the protocol outlined in Example 4, a stable emulsion could be obtained dissolving 3 g Admul™ W 1403 in 87.5 g soy oil and adding 75 g of the aqueous phase specified under 6a.

6c. Dilution of the ascorbic acid/oil emulsion in fat

The emulsions are intended to be used after dilution in oil or liquified fat. The diluted emulsion is sprayed over the pelleted or extruded feed. To mix the emulsion with the fat, 100 ml of the emulsion (6b) was added to 100 ml of soy oil after which the liquid was thoroughly hand mixed.

6d. Mixing of the ascorbic acid/fat emulsion and the aqueous ascorbic acid solution with broiler finisher feed Starting from either the ascorbic acid fat emulsion or the aqueous ascorbic acid solution, equal quantities of ascorbic acid (200 ppm final concentration) were applied to broiler finisher feed pellets obtained from a local supplier. To that end 200 ml of the oil emulsion was sprayed on 10 kg of feed pellets rotating in a concrete mixer. Similarly, 50 ml of the aqueous ascorbic acid mixture (6a) was sprayed on 10 kg of feed pellets rotating in the concrete mixer. Then an additional Quantity of 100 ml soy oil was sprayed on the same pellets. Immediately after spraying and subsequent sampling, the samples were analysed for ascorbic acid plus dehydro ascorbic acid.

6e. Analysis of ascorbic acid in broiler finisher feed

Ascorbic acid plus dehydro ascorbic acid were analysed using the dehydro ascorbic/ascorbic acid test as described in: Methods of Biochemical Analysis and Food Analysis using Single Reagents (Boehringer Mannheim, 1989).

10 g of pellets were extracted with 10 ml of acetone for 10 min (to dissolve the fatty material), after which 90 ml of demi water containing 1 g/l Na-EDTA was added. After mixing the pellets and aqueous phase in the Ultra Turrax for 1 min, the samples were centrifuged. Using kit No. 409677 (Boehringer Mannheim), the levels of ascorbic acid and dehydro ascorbic acid in the supernatant were determined.

From the pellets sprayed with the aqueous ascorbic acid solution, 20% of the ascorbic acid could be recovered. In contrast, from the pellets sprayed with the diluted ascorbic acid/oil emulsion, 90% of the ascorbic acid was recovered. This illustrates the protective effect conferred by the emulsion on ascorbic acid stability in a feed preparation.

It is claimed:

1. A water-in-oil emulsion that is stable upon storage for at least one month comprising 1) water, oil, an enzyme, a water activity-lowering polyol and an emulsifier, wherein the enzyme is present in the water phase of the emulsion at a concentration of 0.01–30% w/w, and 2) the polyol water activity-lowering agent is present in the water phase at a concentration of at least 30–70% w/w, which is effective to stabilize the enzyme, wherein said oil component is provided at a ratio of oil to water from 5:1 to 1:1; and wherein said emulsifier is active in the presence of said polyol and wherein said oil is animal, vegetable or mineral oil.

2. The emulsion of claim 1 wherein the polyol is selected from the group consisting of glycerol, sorbitol, sucrose, polypropylene glycol, lactose, trehalose, maltodextrin and glucose.

3. The emulsion of claim 1 wherein the emulsifier is a monoglyceride or is a polyglycerol polyricinoleate.

4. The emulsion of claim 1 wherein the enzyme is a protease, a carbohydrase, a lipase, a phospholipase, an oxidoreductase, or a phytase.

5. A method for preparing a foodstuff which method comprises adding to the ingredients of said foodstuff the emulsion of claim 1.

6. The method of claim 5 wherein said foodstuff is in the form of particles and wherein said method comprises spraying said particles with said emulsion.

7. An animal or human food comprising the emulsion of any of claims 1, 2, 3 and 4.

8. A cosmetic preparation comprising the emulsion of any of claims 1, 2, 3 and 4.

\* \* \* \* \*